United States Patent
Schafer et al.

(10) Patent No.: US 10,825,149 B2
(45) Date of Patent: Nov. 3, 2020

(54) DEFECTIVE PIXEL CORRECTION USING ADVERSARIAL NETWORKS

(71) Applicant: Siemens Healthcare GmbH, Erlangen (DE)

(72) Inventors: Sebastian Schafer, Madison, WI (US); Kevin Royalty, Fitchburg, WI (US); Olivier Pauly, Munich (DE)

(73) Assignee: Siemens Healthcare GmbH, Erlangen (DE)

( * ) Notice: Subject to any disclaimer, the term of this patent is extended or adjusted under 35 U.S.C. 154(b) by 121 days.

(21) Appl. No.: 16/110,282

(22) Filed: Aug. 23, 2018

(65) Prior Publication Data

US 2020/0065945 A1 Feb. 27, 2020

(51) Int. Cl.
| | |
|---|---|
| *G06K 9/40* | (2006.01) |
| *G06T 5/00* | (2006.01) |
| *G06T 5/50* | (2006.01) |
| *G06T 7/00* | (2017.01) |
| *A61B 6/00* | (2006.01) |

(52) U.S. Cl.
CPC ............... *G06T 5/005* (2013.01); *G06T 5/50* (2013.01); *G06T 7/0014* (2013.01); *A61B 6/5258* (2013.01); *G06T 2207/20081* (2013.01)

(58) Field of Classification Search
CPC ......... G06T 5/005; G06T 5/50; G06T 7/0014; G06T 2207/20081; A61B 6/5258
USPC ...................................................... 382/254
See application file for complete search history.

(56) References Cited

U.S. PATENT DOCUMENTS

| | | | |
|---|---|---|---|
| 2013/0051516 A1 | 2/2013 | Yang et al. | |
| 2015/0238148 A1 | 8/2015 | Georgescu et al. | |
| 2016/0048741 A1 | 2/2016 | Nguyen et al. | |
| 2016/0093048 A1 | 3/2016 | Cheng et al. | |
| 2017/0372155 A1* | 12/2017 | Odry | ........................ G06K 9/03 |
| 2017/0372193 A1* | 12/2017 | Mailhe | ................ G06N 3/0472 |
| 2018/0260957 A1* | 9/2018 | Yang | .................... G06T 7/0012 |
| 2018/0288431 A1* | 10/2018 | Liu | ...................... H04N 19/521 |
| 2018/0322366 A1* | 11/2018 | Lim | ..................... G06K 9/6256 |
| 2019/0046068 A1 | 2/2019 | Ceccaldi | ............ G06K 9/6268 |
| 2019/0096056 A1* | 3/2019 | Giering | ................ G06T 7/0006 |
| 2019/0128989 A1* | 5/2019 | Braun | .................... G06N 3/084 |
| 2019/0197358 A1* | 6/2019 | Madani | ............... G06K 9/6267 |
| 2019/0197670 A1* | 6/2019 | Ferrer | ................ G06K 9/00281 |
| 2019/0198156 A1* | 6/2019 | Madani | ............... G06N 3/0481 |
| 2019/0236614 A1* | 8/2019 | Burgin | .............. G06Q 30/0185 |
| 2019/0266728 A1* | 8/2019 | Lee | ........................ A61B 6/037 |
| 2019/0369191 A1* | 12/2019 | Gong | ..................... G16H 30/40 |
| 2020/0012896 A1* | 1/2020 | Yoo | ..................... G06K 9/6256 |

* cited by examiner

*Primary Examiner* — Charles T Shedrick (57) ABSTRACT

A framework for defective pixel correction using adversarial networks. In accordance with one aspect, the framework receives first and second training image datasets. The framework performs adversarial training of a corrector and a classifier with the first and second training image datasets respectively. The corrector may be trained to correct a first input image and the classifier may be trained to recognize whether a second input image is real or generated by the corrector. The framework applies the trained corrector to a current image to correct any defective pixels and generate a corrected image. The corrected image may then be presented.

20 Claims, 6 Drawing Sheets

```
initParameters(θ₀^corr)
initParameters(θ₀^class)
For n in [1,nbEpochs]:
    X^real = Sample(X_train^Xray)
    X^gen = GenerateSamples(X_train^Xray, θ_{n-1}^corr)
    # train classifier for nbIters
    θ_n^class = SGD(θ_{n-1}^class, [X^real, X^gen], [Y^real, Y^gen], nbIters)
    # train corrector for nbIters
    X^Xray, Y^Xray = Sample(X_train^Xray)
    θ_n^corr = SGD(θ_{n-1}^corr, [X^Xray, Y^Xray], θ_n^class, nbIters)
```

DEFECTIVE PIXEL CORRECTION USING ADVERSARIAL NETWORKS

TECHNICAL FIELD

The present disclosure generally relates to digital medical data processing, and more particularly to pixel correction using adversarial networks.

BACKGROUND

Digital medical images are reconstructed using raw image data obtained from a scanner. One type of scanner is a flat panel detector, which is a solid-state X-ray digital radiography device. To obtain the image data, X-rays are passed through the subject being imaged and sensed by the flat panel detector. Flat-panel detectors are more sensitive and faster than other types of imaging, such as film. However, bad, failing or broken (i.e., "defective") pixels in the flat panel detector may result in ring artifacts in reconstructed volumetric images, thereby compromising image quality.

Such "bad pixel" problem may be solved by two different approaches. In a first approach, when a detector is delivered or during required maintenance, a service engineer performs a number of test image acquisitions with varying detector exposures to determine and calibrate the detector for offset, gain and defective (or bad) pixels. While detector offset and gain vary only minimally with time, the failure of detector elements resulting in defective image pixels frequently occurs. A defective pixel map may be created for each detector to identify defective pixels. However, it is too time-consuming to calibrate each detector for every failing element.

Another approach is to correct pixels (or voxels) in the volumetric image reconstructed from the raw image data. The bad pixels are represented as dark or bright circles or artifacts in the reconstructed image. Different methods may be used to identify these ring-like structures and interpolate the corrupt image data. However, this 'after the fact' processing approach presents the challenges of misidentifying these artifacts and interpolating larger areas of the reconstructed image.

SUMMARY

Described herein is a framework for pixel identification using adversarial networks. In accordance with one aspect, the framework receives first and second training image datasets. The framework performs adversarial training of a corrector and a classifier with the first and second training image datasets respectively. The corrector may be trained to correct a first input image and the classifier may be trained to recognize whether a second input image is real or generated by the classifier. The framework applies the trained corrector to a current image to correct any defective pixels and generate a corrected image. The corrected image may then be presented.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed; on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to x-ray radiographs, MRI, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images and voxels for 3D images). The image may be, for example, a medical image of a subject collected by computer tomography, magnetic resonance imaging, ultrasound, or any other medical imaging system known to one skilled in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture or a 3D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, and "voxels" for volume image elements, often used with respect to 3D imaging, can be used interchangeably. It should be noted that the 3D volume image is itself synthesized from image data obtained as pixels on a 2D sensor array and displayed as a 2D image from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel" or "subject voxel" are used to indicate a particular image element as it is operated upon using techniques described herein.

Recent advances in machine vision based on deep learning (e.g., deep neural networks or deep convolutional neural networks) and massive training sets (e.g., ImageNet) gathered a lot of attention and attracted a lot of investment. Indeed, they are now reaching so-called superhuman performances for tasks such as natural image classification. Such technology can also be applied to the medical image analysis field to, for example, detect and segment organs and anatomical structures. The benefits of applying such systems in the context of image acquisition quality control and correction can be tremendous, as it will enable detection of defective pixels directly from a patient image and correction of images on the fly.

Figure 1:
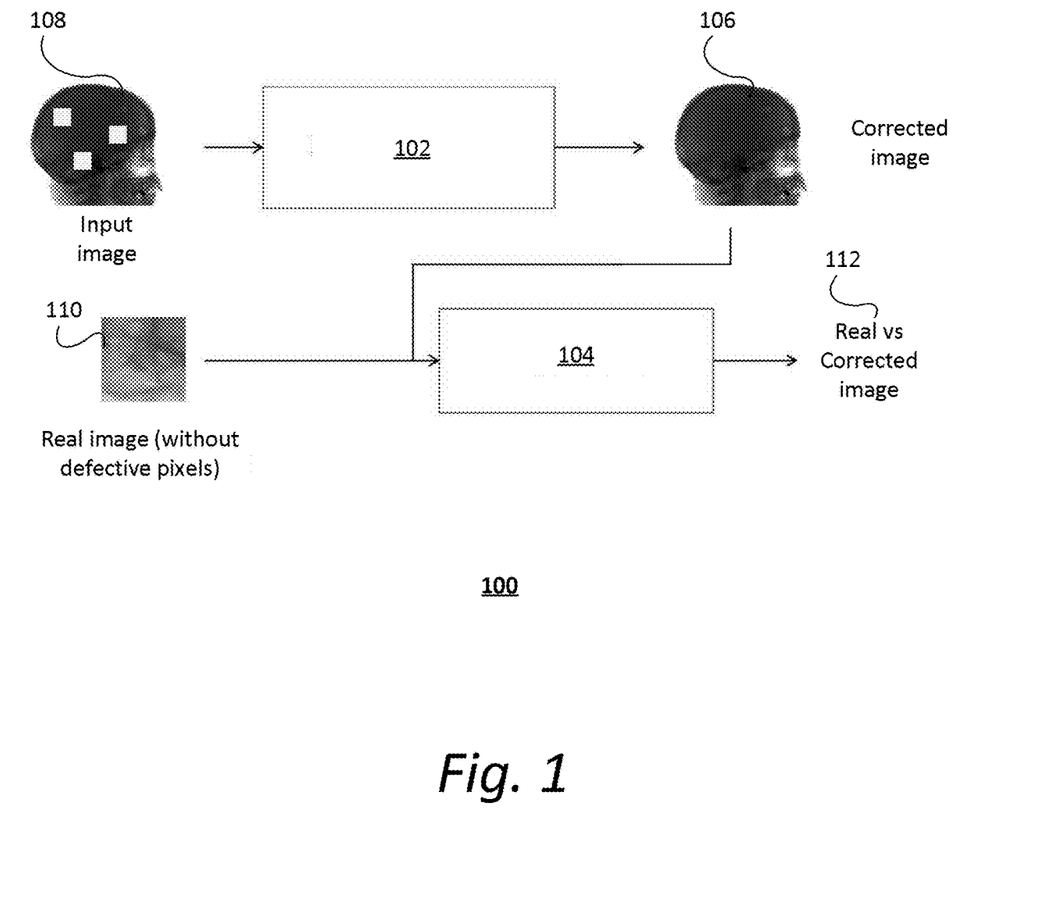
FIG. 1 shows an exemplary defective pixel correction pipeline.

The present framework is based on deep convolutional adversarial networks. The framework makes use of adversarial training to ensure that the corrected image preserves higher order structures. FIG. 1 shows an exemplary defective pixel correction pipeline 100. The pipeline 100 includes an image corrector 102 and a classifier 104. Image corrector 102 may be implemented using, for example, a two-dimensional (2D) deep convolutional network for pixel correction. Image corrector 102 may serve to generate a 2D image 106 in which defective pixels have been corrected given an input image 108 with defective pixels. Classifier 104 may be implemented using, for example, a 2D deep convolutional network for recognizing synthetic images from real images. Classifier 104 may serve to generate detection results 112 that indicate whether an input image is generated by the corrector 102 or it is a real image 110 without any defective pixels.

Advantageously, the framework enables online defective pixel correction, resulting in superior 3D image reconstruction quality, reduced service engineer onsite time and improved customer satisfaction compared to standard techniques. These and other features and advantages will be described in more details herein.

Figure 2:
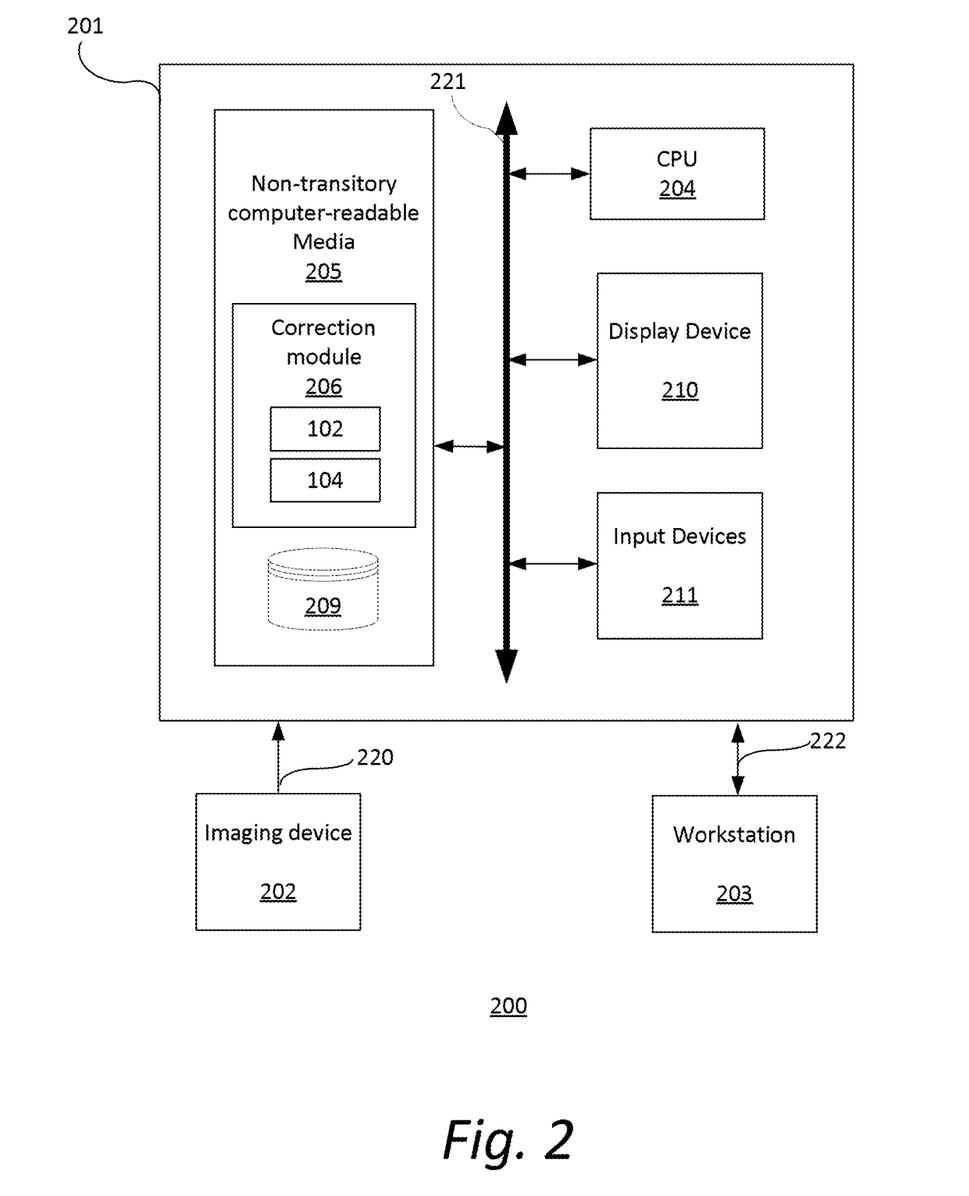
FIG. 2 is a block diagram illustrating an exemplary system.

FIG. 2 is a block diagram illustrating an exemplary system 200. The system 200 includes a computer system 201 for implementing the framework as described herein. In some implementations, computer system 201 operates as a standalone device. In other implementations, computer system 201 may be connected (e.g., using a network) to other machines, such as imaging device 202 and workstation 203. In a networked deployment, computer system 201 may operate in the capacity of a server (e.g., thin-client server), a cloud computing platform, a client user machine in server-client user network environment, or as a peer machine in a peer-to-peer (or distributed) network environment.

In some implementations, computer system 201 comprises a processor or central processing unit (CPU) 204 coupled to one or more non-transitory computer-readable media 205 (e.g., computer storage or memory), display device 210 (e.g., monitor) and various input devices 211 (e.g., mouse or keyboard) via an input-output interface 221. Computer system 201 may further include support circuits such as a cache, a power supply, clock circuits and a communications bus. Various other peripheral devices, such as additional data storage devices and printing devices, may also be connected to the computer system 201.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in non-transitory computer-readable media 205. In particular, the present techniques may be implemented by a correction module 206 and a database 209. The correction module 206 may include an image corrector 102 and a classifier 104, as previously discussed.

Non-transitory computer-readable media 205 may include random access memory (RAM), read-only memory (ROM), magnetic floppy disk, flash memory, and other types of memories, or a combination thereof. The computer-readable program code is executed by CPU 204 to process medical data retrieved from, for example, imaging device 202. As such, the computer system 201 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 205 may be used for storing a database (or dataset) 209. Such data may also be stored in external storage or other memories. The external storage may be implemented using a database management system (DBMS) managed by the CPU 204 and residing on a memory, such as a hard disk, RAM, or removable media. The external storage may be implemented on one or more additional computer systems. For example, the external storage may include a data warehouse system residing on a separate computer system, a cloud platform or system, a picture archiving and communication system (PACS), or any other hospital, medical institution, medical office, testing facility, pharmacy or other medical patient record storage system.

Imaging device 202 acquires medical image data 220 associated with at least one patient. Such medical image data 220 may be processed and stored in database 209. Imaging device 202 may be a radiology scanner (e.g., X-ray, MR or a CT scanner) and/or appropriate peripherals (e.g., keyboard and display device) for acquiring, collecting and/or storing such medical image data 220.

The workstation 203 may include a computer and appropriate peripherals, such as a keyboard and display device, and can be operated in conjunction with the entire system 200. For example, the workstation 203 may communicate directly or indirectly with the imaging device 202 so that the medical image data acquired by the imaging device 202 can be rendered at the workstation 203 and viewed on a display device. The workstation 203 may also provide other types of medical data 222 of a given patient. The workstation 203 may include a graphical user interface to receive user input via an input device (e.g., keyboard, mouse, touch screen voice or video recognition interface, etc.) to input medical data 222.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 3:
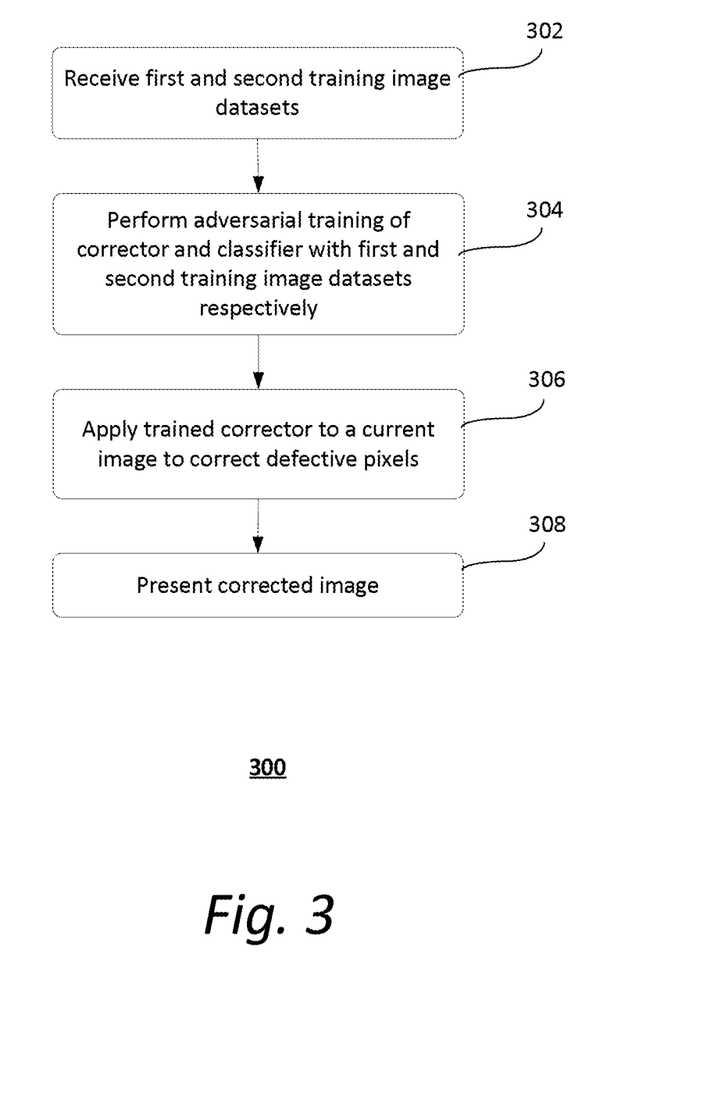
FIG. 3 shows an exemplary method of defective pixel correction by a computer system.

FIG. 3 shows an exemplary method 300 of defective pixel correction by a computer system. It should be understood that the steps of the method 300 may be performed in the order shown or a different order. Additional, different, or fewer steps may also be provided. Further, the method 300 may be implemented with the system 201 of FIG. 2, a different system, or a combination thereof.

At 302, correction module 206 receives first and second training image datasets. The first training image dataset may be used to train corrector 102, while the second training image dataset may be used to train classifier 104. The images in first and second training image datasets may be acquired, directly or indirectly, by using techniques such as high-resolution computed tomography (HRCT), magnetic resonance (MR) imaging, computed tomography (CT), helical CT, X-ray, angiography, positron emission tomography (PET), fluoroscopy, ultrasound, single photon emission computed tomography (SPECT), or a combination thereof. For example, the images in first and second training image datasets may include two-dimensional X-ray images acquired by a flat panel detector.

The images in the first training dataset may be associated with their segmentation masks delineating defective pixels and corrected images. The second training dataset include both real images and synthetic images generated by corrector 102, as well as their associated labels (e.g., "0" if synthetic and "1" if real). The synthetic images in the second training set may be generated by the corrector 102 on the fly during training (i.e., not prepared prior to training) and may be renewed at each training iteration. The real images are original images that contain no defective pixels and are acquired directly from an imaging device 202 without further processing.

Figure 4:
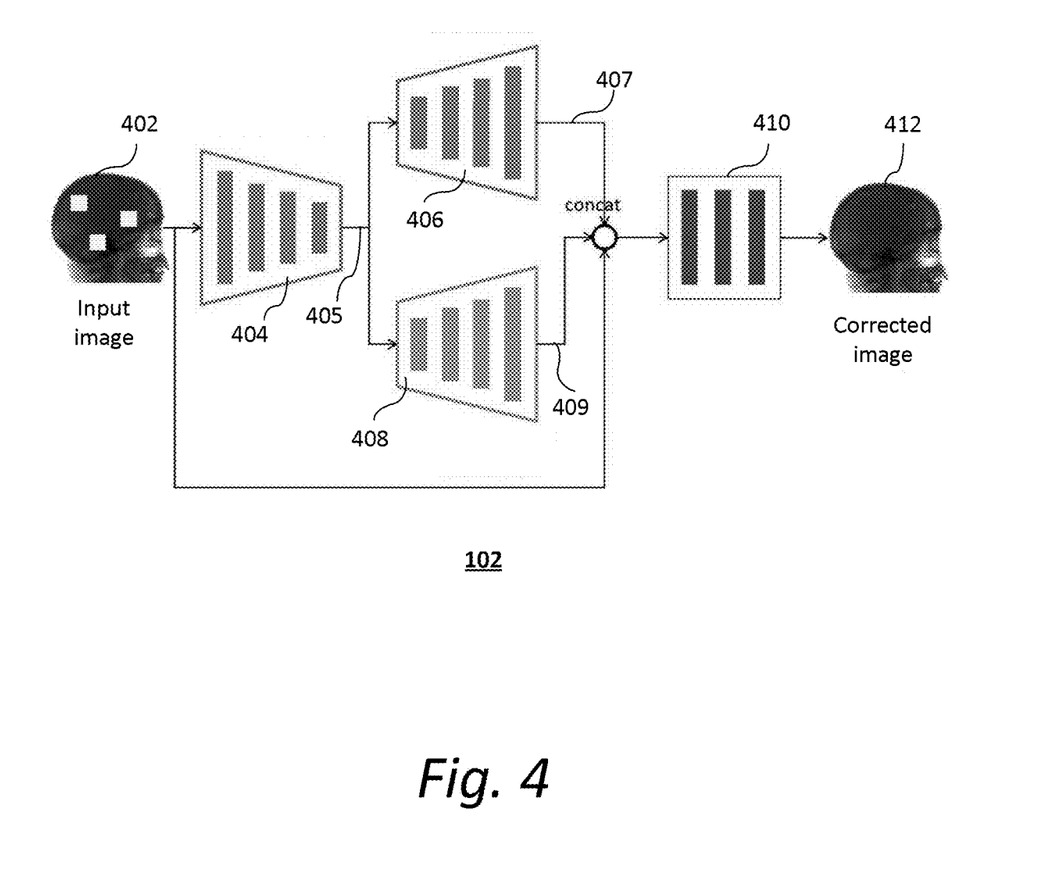
FIG. 4 shows an exemplary corrector.

At 304, correction module 206 performs adversarial training of corrector 102 and classifier 104 with first and second training image datasets respectively. In some implementations, the corrector 102 includes a deep convolutional network. FIG. 4 shows an exemplary corrector 102. The corrector 102 is trained to take as input an image 402 with defective pixels and generate a corrected image 412. The exemplary corrector 102 may include an encoder subnetwork 404, a defective pixel detector subnetwork 406, a raw correction subnetwork 408 and a fusion subnetwork 410.

Encoder subnetwork 404 is a set of convolutional blocks (e.g., 2D convolutional blocks) that contain convolutional, non-linear activations, batch normalization, pooling layers. It may also contain one or more skip connections that connect earlier layers to later ones, or one or more dense connections that connect all layers without any loss of generality. It may also contain one or more inception modules having parallel convolutional blocks. It takes as input the original image 402 and outputs a set of feature channels 405.

Defective pixel detector subnetwork 406 is a set of convolutional blocks (e.g., 2D convolutional blocks) that contain convolutional, non-linear activations, batch normalization and upsampling layers. This layer 406 takes as input the set of feature channels 405 provided by the encoder subnetwork 404 and outputs a probabilistic map 407 that encode the locations of the defective pixels.

Raw correction subnetwork 408 is a set of convolutional blocks (e.g., 2D convolutional blocks) that contain convolutional, non-linear activations, batch normalization and upsampling layers. This layer 408 takes as input the set of feature channels 405 provided by the encoder subnetwork 404 and outputs an image 409 in which defective pixels are corrected.

Fusion subnetwork 410 is a set of convolutional blocks (e.g., 2D convolutional blocks) that contain convolutional, non-linear activations and batch normalization layers. This layer 410 takes as input the input image 402, the output 407 of the defective pixel detector subnetwork 406 as well as the output 409 of the raw correction subnetwork 408. It outputs a corrected image 412 in which defective pixels are corrected.

Alternatively, corrector 102 may include only the encoder subnetwork 404, the defective pixel detector subnetwork 406 and the raw correction subnetwork 408 (i.e. without the fusion network 410). In such implementation, the corrected image may be a linear combination of the original image 402 and the output of the raw correction subnetwork 408 weighted by the probabilistic output of the defective pixel detector subnetwork 406.

Figure 5:
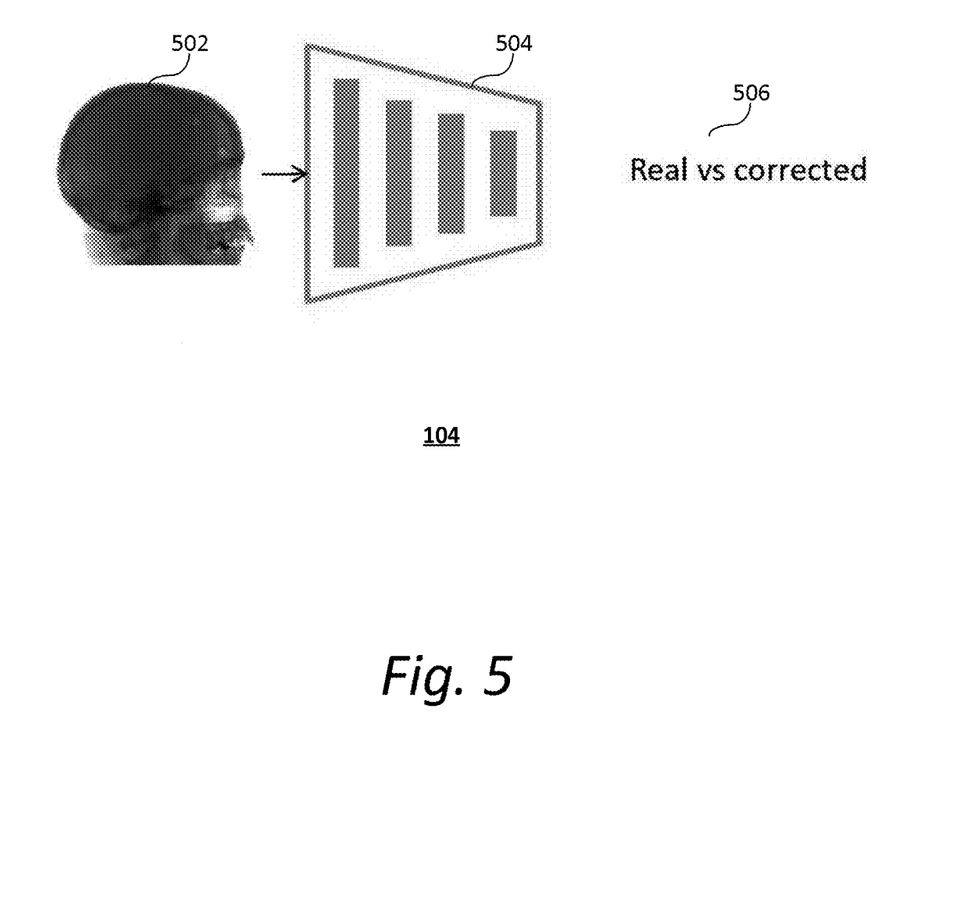
FIG. 5 shows an exemplary classifier.

Classifier 104 is trained to classify input images as being a real image without any defects or a synthetic or corrected image generated by corrector 102. FIG. 5 shows an exemplary classifier 104. Classifier 104 may include a deep convolutional network 504. In some implementations, the deep convolutional network 504 includes a set of convolutional blocks (e.g., 2D convolutional blocks) that contains 2D convolutional, non-linear activations, batch normalization and pooling layers. It may also contain some skip connections that connect earlier layers to later ones, or dense connections that connect all layers without any loss of generality. It may also contain one or more inception modules having parallel convolutional blocks. The input image 502 may be a corrected image generated by corrector 102 or a real image. Classifier may output a probability 506 of the image 502 being a real image.

Corrector 102 and classifier 104 may be trained by using an adversarial training strategy. For example, both the corrector 102 and classifier 104 may be trained simultaneously, with the goal of the corrector 102 being to produce a corrected image that looks as real as possible, and the goal of the classifier 104 being to recognize whether an input image is real or generated by the classifier 102 (i.e., synthetic). The goal of the adversarial training is to minimize the overall loss functions for both the corrector 102 and the classifier 104.

Considering a set of N 2D X-ray images (or patches) and their associated labels $y_n$, (0 if synthetic and 1 if real), the classifier loss function may be defined as a classical binary cross-entropy:

$$L_{classifier} = \frac{1}{N} \cdot \left( \sum_{n=1}^{N} (y_n \log(\widehat{y_n}) + (1 - y_n) \cdot \log(1 - \widehat{y_n})) \right) \quad (1)$$

wherein $\widehat{y_n}$ is the probability provided by the classifier 104 of the input image being a real X-ray image. The goal of the classifier 104 is to learn to distinguish perfectly between a generated (or synthetic) image and a real X-ray image.

Considering a set of N X-ray images denoted by $X_n$, their associated defective pixel segmentation masks $M_n$, and their associated corrected versions $C_n$, the loss function for the corrector 102 may be defined as a weighted summation of a difference term $L_{diff}$, a segmentation term $L_{seg}$ and an adversarial term $L_{adversarial}$ as follows:

$$L_{corrector} = \alpha \cdot L_{diff} + \beta \cdot L_{seg} + \gamma \cdot L_{adversarial} \quad (2)$$

wherein $\alpha$, $\beta$, $\gamma$ are weights for controlling the trade-off between the different terms.

The difference term $L_{diff}$ drives the optimization so that the generated X-ray image looks like the corrected version of the X-ray image using local mean or median filtering. The difference term $L_{diff}$ may be defined as follows:

$$L_{diff} = \frac{1}{N} \cdot \left( \sum_{n=1}^{N} (C_n - \text{Corrector}(X_n))^2 \right) \quad (3)$$

wherein Corrector( ) is the corrector function.

The segmentation term $L_{seg}$ drives the optimization so that the corrector 102 is also able to segment the defective pixels through its detector branch. A segmentation loss function, such as the Dice, Jaccard or Tversky loss function, may be used. As an example, the segmentation term $L_{seg}$ may be defined based on a Dice-like loss function that may be used is as follows:

$$L_{seg} = 1 - \frac{2}{N} \cdot \left( \sum_{n=1}^{N} \frac{\sum_{pixels} Seg(X_n) \cdot M_n}{\sum_{pixels} Seg(X_n) + \sum_{pixels} M_n} \right) \quad (4)$$

wherein Seg( ) is the segmentation function (e.g., output of the defective pixel detector subnetwork 406).

Finally, the adversarial term $L_{adversarial}$ drives the optimization so that the image generated by the corrector 102 fools the classifier 104 and gets classified as "real". The adversarial term $L_{adversarial}$ may be defined as follows:

$$L_{adversarial} = \frac{1}{N} \cdot \sum_{n=1}^{N} \log(\text{Class}(\text{Corrector}(X_n))) \quad (5)$$

wherein Class( ) is the classifier function.

Figure 6:
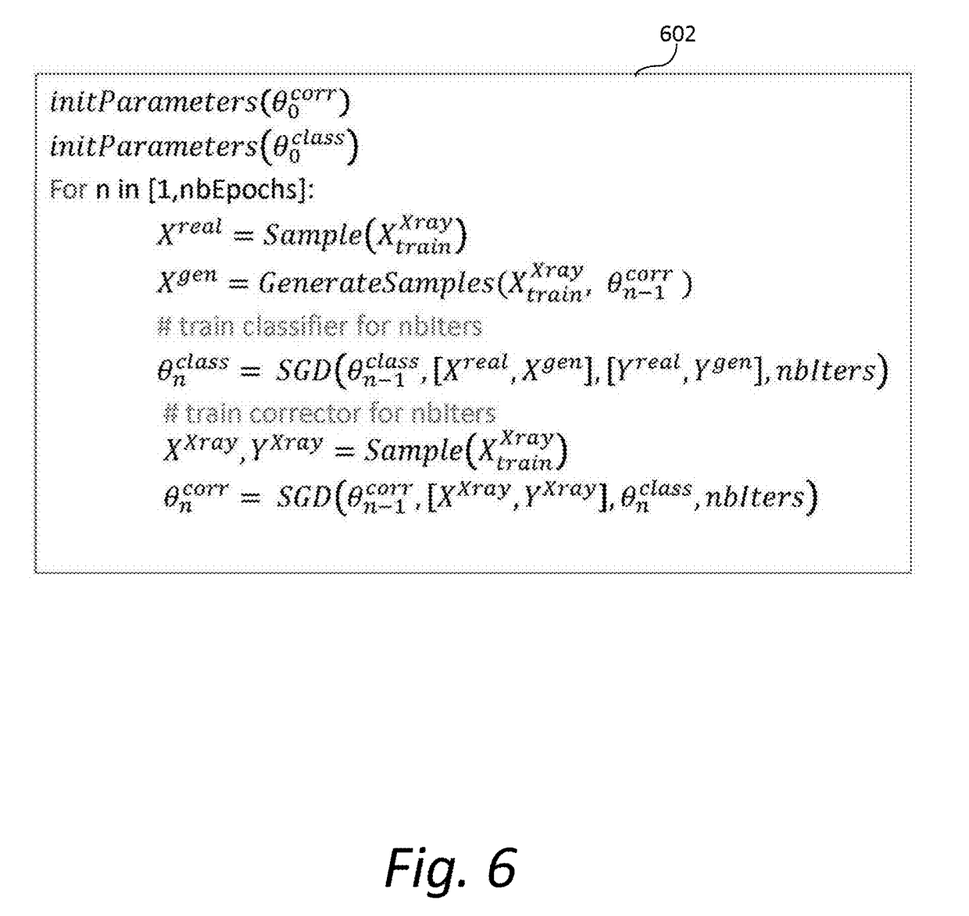
FIG. 6 shows the exemplary pseudo-code for training the corrector and the classifier.

FIG. 6 shows the exemplary pseudo-code 602 for training the corrector 102 and the classifier 104. For a given number of epochs (nbEpochs), the classifier 104 and the corrector 102 may be trained simultaneously. During one epoch, the classifier 104 ($\theta^{class}$) may be trained given a batch of real and corrected (or synthetic) images for a certain number of iterations (nbIters). Afterwards, the corrector 102 ($\theta^{corr}$) may be trained for a certain number of iterations by computing the predictions of the classifier 104 using the current state of the classifier 104. Classical optimizers, such as Stochastic Gradient Descent (SGD) or Adam, may be used to train the corrector 102 and the classifier 104.

Returning to FIG. 3, at 306, correction module 206 applies the trained corrector 102 to a current image to correct defective pixels. The trained classifier 104 may be discarded once training is completed. The current image may be a radiographic image (2D X-ray image) of a patient. The current image may be acquired by, for example, imaging device 202, using the same modality (e.g., flat panel detector) as that used to acquire the first and second training image datasets. Trained corrector 102 may be used for correcting unseen or new current images. Forward propagation may be performed through the trained corrector 102 to generate the corrected image. A probabilistic map representing the defective pixels may also be generated. Each value in the probabilistic map may represent the probability of the corresponding pixel being defective.

At 308, correction module 206 presents the corrected image. The corrected image may be displayed to the user at, for example, workstation 203. The probabilistic map may also be displayed. For example, the probabilistic map may be overlaid onto the corrected image and displayed as a heatmap. Alternatively, or additionally, the probabilistic map may be used to generate a notification (e.g., text message, electronic mail) to the relevant personnel for maintenance of the imaging device 202. For example, if any of the values in the probabilistic map exceeds a predetermined threshold, the technician may be notified to perform maintenance on the imaging device used to acquire the current image.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. One or more non-transitory computer readable media embodying a program of instructions executable by machine to perform operations for defective pixel correction, the operations comprising:
receiving first and second training image datasets;
performing adversarial training of a corrector and a classifier with the first and second training image datasets respectively, wherein the corrector comprises a defective pixel detector subnetwork and a raw correction subnetwork, wherein the defective pixel detector subnetwork is trained to encode one or more locations of one or more defective pixels of a first input image, wherein the raw correction subnetwork is trained to correct the one or more defective pixels in the first input image, wherein the classifier is trained to recognize whether a second input image is real or generated by the corrector;

applying the trained corrector to a current image to generate a corrected image; and presenting the corrected image.

2. The one or more non-transitory computer readable media of claim 1 wherein the current image comprises a two-dimensional X-ray image.

3. The one or more non-transitory computer readable media of claim 1 wherein the corrector and the classifier comprise two-dimensional deep convolutional networks.

4. The one or more non-transitory computer readable media of claim 1 wherein the corrector further comprises an encoder subnetwork that provides a set of feature channels based on the first input image to the defective pixel detector subnetwork and the raw correction subnetwork.

5. A system comprising:
a non-transitory memory device for storing computer readable program code; and
a processor in communication with the memory device, the processor being operative with the computer readable program code to perform operations including
receiving first and second training image datasets,
performing adversarial training of a corrector and a classifier with the first and second training image datasets respectively, wherein the corrector comprises a defective pixel detector subnetwork and a raw correction subnetwork, wherein the defective pixel detector subnetwork is trained to encode one or more locations of one or more defective pixels of a first input image, wherein the raw correction subnetwork is trained to correct the one or more defective pixels in the first input image, wherein classifier is trained to recognize whether a second input image is real or generated by the corrector,
applying the trained corrector to a current image to generate a corrected image, and
presenting the corrected image.

6. The system of claim 5 wherein the first training image dataset comprises images associated with segmentation masks delineating defective pixels.

7. The system of claim 5 wherein the second training image dataset comprises real images acquired directly from an imaging device and synthetic images generated by the corrector.

8. The system of claim 5 wherein the corrector comprises a deep convolutional network.

9. The system of claim 5 wherein the corrector further comprises an encoder subnetwork that provides a set of feature channels based on the first input image to the defective pixel detector subnetwork and the raw correction subnetwork.

10. The system of claim 9 wherein the corrected image is a linear combination of the first input image and an output of the raw correction subnetwork weighted by a probabilistic output of the defective pixel detector subnetwork.

11. The system of claim 9 wherein the corrector further comprises a fusion subnetwork that outputs the corrected image.

12. The system of claim 11 wherein the fusion subnetwork takes as input the first input image, an output of the defective pixel detector subnetwork and an output of the raw correction subnetwork.

13. The system of claim 5 wherein the classifier comprises a deep convolutional network.

14. The system of claim 13 wherein the deep convolutional network comprises two-dimensional convolutional blocks.

15. The system of claim 5 wherein the processor is operative with the computer readable program code to simultaneously train the corrector and the classifier to minimize a corrector loss function and a classifier loss function.

16. The system of claim 15 wherein the classifier loss function comprises a binary cross-entropy function.

17. The system of claim 15 wherein the corrector loss function comprises a weighted summation of a difference term, a segmentation term and an adversarial term.

18. The system of claim 5 wherein the processor is operative with the computer readable program code to perform adversarial training by training the classifier and the corrector simultaneously for multiple epochs, wherein during one of the epochs, the classifier is iteratively trained given a batch of real and synthetic images and the corrector is iteratively trained using a current state of the classifier.

19. A method, comprising:
receiving first and second training image datasets;
performing adversarial training of a corrector and a classifier with the first and second training image datasets respectively, wherein the corrector comprises a defective pixel detector subnetwork and a raw correction subnetwork, wherein the defective pixel detector subnetwork is trained to encode one or more locations of one or more defective pixels of a first input image, wherein the raw correction subnetwork is trained to correct the one or more defective pixels in the first input image, wherein the classifier is trained to recognize whether a second input image is real or generated by the corrector;
applying the trained corrector to a current image to generate a corrected image; and
presenting the corrected image.

20. The method of claim 19 wherein applying the trained corrector to the current image further comprises generating a probabilistic map representing the defective pixels.

* * * * *